United States Patent [19]

Durand et al.

[11] Patent Number: 5,434,323
[45] Date of Patent: Jul. 18, 1995

[54] METHOD FOR REDUCING THE AGGLOMERATION TENDENCY OF HYDRATES IN PRODUCTION EFFLUENTS

[75] Inventors: Jean-Pierre Durand, Chatou; Patrick Gateau, Maurepas; Baley: Anne-Sophie, Paris; Andre Sugier, Rueil Malmaison, all of France

[73] Assignee: Institut Francais du Petrole, Rueil Malmaison, France

[21] Appl. No.: 101,167

[22] Filed: Aug. 3, 1993

[30] Foreign Application Priority Data

Aug. 3, 1992 [FR] France .................... 92 09686

[51] Int. Cl.⁶ .................... F17D 1/05; C10G 33/04
[52] U.S. Cl. .................... 585/15; 208/187; 208/188; 95/153
[58] Field of Search ............ 208/187, 188; 585/15, 585/867; 95/153

[56] References Cited

U.S. PATENT DOCUMENTS 5,244,878  9/1993  Sugier et al. .................... 507/90

FOREIGN PATENT DOCUMENTS 0323774  7/1989  European Pat. Off. .
2131820  6/1984  United Kingdom .

Primary Examiner—Asok Pal
Assistant Examiner—Bekir L. Yildirim
Attorney, Agent, or Firm—Millen, White, Zelano, & Branigan

[57] ABSTRACT

The invention relates to a process for reducing the agglomeration tendency of hydrates within a fluid containing water and gas by adding a nonionic, amphiphilic compound obtained by reacting at least one polyalkenylsuccinic anhydride or acid with a polyethylene glycol monoether. The nonionic, amphiphilic compound is generally introduced in a concentration of 0.1 to 5% by weight, based on the water present.

12 Claims, No Drawings

METHOD FOR REDUCING THE AGGLOMERATION TENDENCY OF HYDRATES IN PRODUCTION EFFLUENTS

BACKGROUND OF THE INVENTION

The invention relates to a process for reducing the agglomeration tendency of the hydrates of natural gas, petroleum gas or other gases, by the use of at least one additive. The gases which form hydrates can in particular incorporate at least one hydrocarbon chosen from among methane, ethane, ethylene, propane, propene, n-butane and isobutane and optionally $H_2S$ and/or $CO_2$.

These hydrates form when water exists in the presence of gas, either in the free state, or in the state dissolved in a liquid phase, such as a liquid hydrocarbon, and when the temperature reached by the mixture of in particular water, gases and optionally liquid hydrocarbons, such as oil, drops below the thermodynamic hydrate formation temperature, which is given for a known gas composition and when the gas pressure is fixed.

Hydrate formation is feared, particularly in the petroleum and gas industries, where the hydrate formation conditions can occur. Thus, in order to reduce the costs of the production of crude oil and gas, both from the investment standpoint and from the standpoint of exploitation, one procedure envisaged, particularly in the case of ocean production, is to reduce or eliminate the treatments applied to the crude or gas to be transported from the field to the coast and in particular all or part of the water is left in the fluid to be transported. These ocean treatments generally take place on a platform on the surface close to the field in such a way that the initially hot effluent can be treated prior to the thermodynamic hydrate formation conditions being reached as a result of the cooling of the effluent with the sea water.

However, as occurs in practice, when the requisite thermodynamic conditions for the formation of hydrates occur, the agglomeration of the hydrates leads to the filling and blocking of the transportation pipes as a result of the formation of plugs, which prevent any passage of crude or gas.

The formation of hydrate plugs can stop production and therefore cause significant financial losses. Moreover, the restoration to service of the installation, particularly in the case of ocean production or transportation may be far from easy, because it is very difficult to decompose the hydrates formed. Thus, when the production of an underwater deposit of natural gas or petroleum and gas containing water reaches the surface and is then transported to the bottom of the ocean, as a result of the lowering of the temperature of the effluent produced, the thermodynamic conditions are obtained for the formation and agglomeration of hydrates, so as to block the transfer pipes. The temperature at the bottom of the ocean can e.g. be 3° or 4° C.

Conditions favorable for hydrate formation can also occur in the same way on land, in the case of pipes which are not buried or not adequately buried in the ground, e.g. when the ambient air temperature is low.

To avoid these disadvantages, the prior art has sought to use products which, added to the fluid, could act as inhibitors by lowering the thermodynamic hydrate formation temperature. These are in particular alcohols such as methanol, or glycols, such as mono, di or triethylene glycol. This solution is very onerous, because the quantity of inhibitors to be added can reach 10 to 30% of the water content and these inhibitors are difficult to recover in a complete manner.

There has also been a recommendation to isolate the transfer pipes, so as to prevent the temperature of the transported fluid from reaching the hydrate formation temperature under the operating conditions. However, such a procedure is very expensive.

In addition, several nonionic or anionic surfactants have been tested for their effect of delaying the formation of hydrates within a fluid containing a gas, particularly a hydrocarbon and water. Reference can e.g. be made in this connection to the article by Kuliev et al: "Surfactants studied as hydrate - formation inhibitors" Gazovoe Delo, No. 10, 1972, pp. 17-19, reported in Chemical Abstracts 80, 1974, 98122.

A description has also been given of additives able to modify the hydrate formation mechanism, because instead of rapidly agglomerating with one another and forming very solid plugs, the hydrates formed disperse in the fluid without agglomerating and without obstructing the pipes, when the temperature of the transported fluid is not too low.

Reference can be made in this connection to patent application EP-A-323,774 in the name of the present applicant, which describes the use of nonionic, amphiphilic compounds chosen from among esters of polyols and carboxylic acids, in substituted or unsubstituted form and imide function compounds. Patent application EP-A-323 775 in the name of the present applicant, more particularly describes the use of compounds belonging to the group of diethanol amides of fatty acids or fatty acid derivatives. U.S. Pat. No. 4,856,593 describes the use of surfactants such as organic phosphonates, phosphate esters, phosphonic acids, their salts and esters, ionic polyphosphates and their esters, as well as polyacrylamides and polyacrylates. Patent application EP-A-457,375 describes the use of anionic surfactants, such as alkyl aryl sulphonic acids and their alkali metal salts.

SUMMARY OF THE INVENTION

It has now been found that amphiphilic compounds obtained by reacting at least one succinic derivative chosen from within the group formed by polyalkenylsuccinic anhydrides and acids on at least one polyethylene glycol monoether could advantageously be used for reducing the agglomeration tendency of hydrates of natural gas, petroleum gas or other gases.

Therefore the invention proposes a process for the reduction of the agglomeration tendency of hydrates within a fluid containing water and a gas, under conditions where hydrates can form from the water and the gas, characterized in that into said fluid is incorporated an additive containing at least one nonionic, amphiphilic compound obtained by reacting at least one succinic derivative chosen from within the group formed by polyalkenylsuccinic anhydrides and acids on at least one polyethylene glycol ether, the molar proportion of the reagents being 0.5 to 2 and preferably close to 1.

The succinic derivatives used for the preparation of the compounds used in the invention normally have a number average molecular weight of approximately 200 to 5000 and preferably 500 to 2000. These succinic derivatives have been extensively described in the prior art. They are, e.g., obtained by the action of at least one olefin or a chlorinated hydrocarbon on maleic anhydride or acid. The olefin or chlorinated hydrocarbon used in this synthesis can be straight or branched and normally have 10 to 200, preferably 15 to 150 and most frequently 20 to 100 carbon atoms in their molecule. The said olefin can also be an oligomer, e.g. a dimer, trimer or tetramer, or a polymer of a lower olefin having e.g. 2 to 12 carbon atoms, such as ethylene, propylene,.1-butene, isobutene, 1-hexene, 1-octene, 2-methyl-1-heptene, 2-methyl-5-propyl-1-hexene or 1-decene. The chlorinated hydrocarbon can result from the chlorination of such polymers. It is possible to use mixtures of olefins or mixtures of chlorinated hydrocarbons. Advantageously, the succinic derivative used is a polyisobutenyl succinic anhydride.

The polyethylene glycol monoethers used for preparing the compounds used in the invention normally have a number average molecular weight between 100 and 6000 and comply with the following general formula:

$$R = (-O-CH_2-CH_2)_n OH \qquad (1)$$

in which R is a hydrocarbon group e.g. containing 1 to 30 carbon atoms and n, representing the average degree of polymerization, has a value of approximately 2 to 140.

The respective molecular weights of the succinic derivative and the polyethylene glycol monoether in question are advantageously chosen in such a way that the amphiphilic compound resulting from their reaction has a hydrophilic lipophilic balance (HLB) at the most equal to 8 and preferably between 2 and 7. The (HLB) value can be estimated on the basis of the relation.

$$HLB = \frac{E + C}{5}$$

in which E represents the % by weight of ethylene oxide in the molecule and C the % by weight of free carboxyl groups, which also give the molecule a hydrophilic character.

In practice, for preparing the compounds usable according to the invention, use is preferably made of polyethylene glycol methyl monoethers. The reaction between the succinic derivative and the polyethylene glycol monoether is carried out in a solvent such as toluene, xylene or a commercial aromatic fraction at a temperature between e.g. 80° and 200° C.

In their use as additives for reducing the agglomeration tendency of hydrates, these compounds are added to the fluid to be treated at concentrations generally ranging between 0.1 and 5 and preferably 0.25 and 2% by weight, based on the water.

In order to test the effectiveness of the products used in the process according to the invention, the transportation of fluids forming hydrates, such as petroleum effluents, was simulated and the equipment described hereinafter was used for tests concerning the formation of hydrates from gases, condensate and water.

The equipment comprises a 10 meter loop constituted by tubes having an internal diameter of 7.7 mm, a 2 liter reactor having an inlet and an outlet for the gas, a suction means and a delivery means for the mixture, i.e. the condensate, water and additive initially introduced. The reactor makes it possible to place the loop under pressure.

Tubes having a diameter identical to those of the loop are used for ensuring the circulation of the fluids from the loop to the reactor and vice versa by means of a geared pump placed between the two. A sapphire cell integrated into the circuit makes it possible to render visible the circulating liquid and therefore the hydrates if they have formed.

In order to determine the efficiency of the additives according to the invention, the fluids (water, condensate, additive) are introduced into the reactor and the installation is placed under a pressure of 70 bars. The homogenization of the liquids is ensured by their circulation in the loop and the reactor and then solely in the loop. By following the flow rate and pressure drop variations, a rapid temperature drop of 11° C. is imposed on the hydrate formation temperature and the latter is then maintained at this value.

The tests can last for a few minutes to several hours. A high-performance additive makes it possible to maintain the circulation of the hydrate suspension with a stable flow rate and pressure drop.

The following examples illustrate the invention, but in no way limit the scope thereof. Example 3 is given for comparison purposes.

EXAMPLE 1

Into a 50 liter reactor equipped with stirring system and a condenser are introduced 11.4 kg of polyisobutenyl succinic anhydride with an anhydride number of 0.080 anhydride function/100 g dissolved in 16.4 kg of a commercial aromatic fraction having a 99% aromatics content, an initial boiling point of 286° C. and a final boiling point of 214° C. After adding 5.0 kg of polyethylene glycol monomethyl ether, whose average molecular weight is 550, the reaction mixture obtained is stirred for 6 hours at 150° to 160° C., in order to obtain 32.8 kg of a solution containing 50% by weight of semiester. The product has a HLB of 6.6.

EXAMPLE 2

Into the reactor used in Example 1 are introduced 12 kg of polyisobutenyl succinic anhydride having an anhydride number of 0.080 anhydride function/100 g dissolved in 15.36 kg of xylene. After adding 3.36 kg of polyethylene glycol monomethyl ether, whose average molecular weight is 350, the thus obtained reaction mixture is heated at the xylene reflux for 6 hours and 30.72 kg of a solution containing 50% by weight semi-ester is obtained. The product has a HLB of 4.9.

EXAMPLE 3 (comparative)

This example uses a fluid constituted by 10% by volume water and 90% by volume condensate. The weight composition of the condensate is for the molecules having less than 11 carbon atoms, 20% paraffins and isoparaffins, 48% naphthenes and 10% aromatics, and for the molecules having at least 11 carbon atoms 22% of a mixture of paraffins, isoparaffins, naphthenes and aromatics.

The gas used has 98% by volume methane and 2% by volume ethane. The experiment is carried out under a pressure of 7 MPa, kept constant by a supply of gas. Under these conditions a plug is formed in the loop 10 minutes after the start of hydrate formation, the hydrates having formed as blocks.

EXAMPLE 4

This example uses the operating procedure of comparative example 3, using the same fluid, gas and pressure, but adding to the circulating fluid 1% by weight, based on the water, of the product produced in example 1. Under these conditions, there is a rise in the pressure drop during the formation of hydrates at 4° C., followed by its decrease and stabilization for more than 24 hours. A temperature drop to 0° C. does not affect the circulation of the suspension, the hydrates remaining dispersed in the fluids.

EXAMPLE 5

Everything else being equal, example 4 is repeated using 1% by weight, based on the water, of the product prepared in the manner described in example 2. Under these conditions and as in example 4, the circulation of the fluid is maintained for more than 24 hours.

We claim:

1. A process for reducing the agglomeration tendency of hydrates within a fluid containing water and a gas, under conditions where hydrates can form from the water and the gas, said process comprising incorporating into said fluid an additive containing at least one nonionic, amphophilic compound, having a hydrophilic lipophilic balance (HLB) value at the most equal to 8, which compound is the reaction product of at least one succinic derivative which is an alkenylsuccinic acid or anhydride, with at least one polyethylene glycol monoether, the molar ratio of the acid or anhydride/monoether being 0.5 to 2.

2. A process according to claim 1, wherein the molar ratio of the acid or anhydride/monoether is about 1.

3. A process according to claim 1, wherein the succinic acid or anhydride has a number average molecular weight of approximately 200 to 5000 and said polyalkylene glycol monoether has a number average molecular weight of 100 to 6000 and has the formula:

$$R-(-O-CH_2-CH_2-)_n OH$$

in which R is a hydrocarbon group having 1 to 30 carbon atoms and n is the average degree of polymerization and has a value of 2 to 140.

4. A process according to claim 1, wherein said amphophilic compound has a hydrophilic lipophilic balance (HLB) value between 2 and 7.

5. A process according to claim 1, wherein said polyethylene glycol monoether is a polyethylene glycol methyl monoether.

6. A process according to claim 1, wherein the succinic derivative is a polyisobutenyl succinic anhydride with a number average molecular weight of 500 to 2000.

7. A process according to claim 1, wherein said nonionic, amphiphilic compound is incorporated into said fluid at a concentration of 0.1 to 5% by weight, based on the water present.

8. A process according to a claim 7, wherein said concentration is 0.25 to 2% by weight, based on the water present.

9. A process according to claim 1, wherein, in said fluid, the said gas comprises at least one hydrocarbon chosen from among methane, ethane, ethylene, propane, propene, n-butane and isobutane and optionally $H_2S$ and/or $CO_2$.

10. A process according to claim 1, wherein that said fluid comprises natural gas.

11. A process according to claim 1, wherein that said fluid comprises petroleum gas and at least one liquid hydrocarbon.

12. A process according to claim 1, wherein the fluid contains oil, water and a gas.

* * * * *